(12) United States Patent
Yanase et al.

(10) Patent No.: US 7,569,379 B2
(45) Date of Patent: Aug. 4, 2009

(54) PENTOSE-FERMENTATIVE TRANSFORMED ZYMOBACTER MICROORGANISMS (75) Inventors: Hideshi Yanase, Tottori (JP); Kenji Okamoto, Tottori (JP); Takahide Takadera, Ninomiya-machi (JP); Atsuko Sugiura, Yokohama (JP)

(73) Assignee: Kansai Paint Co., Ltd., Amagasaki-shi (JP)

( * ) Notice: Subject to any disclaimer, the term of this patent is extended or adjusted under 35 U.S.C. 154(b) by 604 days.

(21) Appl. No.: 10/901,471

(22) Filed: Jul. 29, 2004

(65) Prior Publication Data

US 2007/0298476 A1 Dec. 27, 2007

(30) Foreign Application Priority Data

Jul. 31, 2003 (JP) ............................. 2003-284163

(51) Int. Cl.
*C12P 7/00* (2006.01)
*C12P 7/06* (2006.01)
*C12N 1/21* (2006.01)

(52) U.S. Cl. .................................... 435/252.3; 435/161
(58) Field of Classification Search ....................... None
See application file for complete search history.

(56) References Cited

U.S. PATENT DOCUMENTS 5,712,133 A    1/1998   Picataggio et al.
6,333,181 B1 * 12/2001  Ingram et al. ............... 435/165

* cited by examiner

*Primary Examiner*—Janet L Epps-Smith
(74) *Attorney, Agent, or Firm*—Wenderoth, Lind & Ponack, L.L.P.

(57) ABSTRACT

This invention provides transformed microorganisms which can produce ethanol from pentose, by introducing pentose metabolizing enzymes into microorganisms belonging to genus *Zymobacter* which cannot utilize pentose.

6 Claims, 3 Drawing Sheets

Fig. 1

ETHANOL SYNTHESIS PATHWAY FROM XYLOSE

Fig. 2

RESTRICTION ENZYME CLEAVAGE MAP OF pUC118-xyl A, B

Fig. 3

RESTRICTION ENZYME CLEAVAGE MAP OF pUC118-*tal+tkt*

Fig. 4

RESTRICTION ENZYME CLEAVAGE MAP OF pMFY31-*xt*

Fig. 5

XYLOSE FERMENTATION BY RECOMBINANT Zymobacter palmae [pMFY31-xf]

Fig. 6

XYLOSE FERMENTATION BY RECOMBINANT Zymobacter palmae

PENTOSE-FERMENTATIVE TRANSFORMED ZYMOBACTER MICROORGANISMS

TECHNICAL FIELD

This invention relates to a recombinant DNA which contains exogenous gene(s) encoding at least one enzyme selected from xylose isomerase, xylulokinase, transaldolase and transketolase; and to transformed microorganisms containing said recombinant DNA fragment(s). Said transformed microorganisms can be utilized for efficient ethanol production from xylose-containing feedstocks.

BACKGROUND ART

In carrying out ethanol production using cellulosic biomass as the feedstock, first the biomass is degraded to monosaccharides and the saccharified solution is used as the substrate for fermentation. Degradation and saccharification of cellulosic biomass are carried out by enzyme process using cellulase or acid saccharification process using sulfuric acid or the like. Whereas, because certain biomasses have high hemicellulose contents besides those of cellulose, their saccharified solutions may contain, besides glucose, hemicellulose-derived xylose. Representative microorganisms used for ethanol production are yeast belonging to genus *Saccharomyces* or bacteria belonging to genus *Zymomonas* or *Zymobacter*. These microorganisms normally produce ethanol efficiently from sugars such as glucose, but are incapable of producing ethanol from xylose. To improve yield in ethanol production from biomass feedstock, therefore, it is necessary to construct a transformed microorganism capable of producing ethanol from xylose substrate, by introducing an enzyme which participates in xylose metabolism into said microorganisms used for ethanol production.

Bacteria of genus *Zymomonas* and genus *Zymobacter* are known to show higher fermentation speed than yeast of genus *Saccharomyces*. For example, U.S. Pat. No. 5,712,133 has disclosed construction of transformed microorganisms which could efficiently produce ethanol from xylose, by transforming *Zymomonas* bacteria to impart thereto pentose fermentation ability. *Zymomonas* bacteria, however, have narrower fermentable sugar range than *Zymobacter* bacteria, and must be transformed with still more genes for fermenting feedstocks comprising maltose, galactose, mannose and the like with high efficiency.

DISCLOSURE OF THE INVENTION

A main object of the present invention is to provide transformed microorganisms which are capable of producing ethanol from pentose, by introducing pentose metabolic enzyme or enzymes into microorganisms belonging to genus *Zymobacter* which are incapable of utilizing pentose, by recombinant DNA method.

We noticed microorganisms which could digest xylose and carried out various screening procedures, to successfully obtain xylose isomerase, xylulokinase, transaldolase and transketolase genes which participate in xylose metabolism. Because no host-vector system with *Zymobacter* bacteria was established then, we made concentrative studies on construction of vectors, transformation method and cloning genes which code enzymes participating in xylose metabolism, to now discover that use of *Zymobacter* bacteria exhibiting broad fermentable sugar range as the host achieves easier adaptation to fermentation feedstock comprising various sugars. The present invention is whereupon completed.

Accordingly, therefore, the present invention provides a transformed *Zymobacter* microorganism into which exogenous gene(s) encoding at least one enzyme selected from xylose isomerase, xylulokinase, transaldolase and transketolase is introduced and which has pentose fermentability, i.e., an ability to produce ethanol from pentose sugars, in particular, xylose, used as the substrate.

The invention also provides recombinant DNA constructed by ligating a DNA fragment with a vector, said DNA fragment being derived from xylose metabolizing enzyme-producing bacterial strain and comprising gene(s) encoding at least one enzyme selected from xylose isomerase, xylulokinase, transaldolase and transketolase.

Hereinafter the present invention is explained in further details.

In the present invention, a microorganism having xylose digesting ability is used as a DNA donor, from which a DNA encoding at least one enzyme selected from xylose isomerase, xylulokinase, transaldolase and transketolase is isolated and purified. Cleaving said DNA by various known methods, a DNA fragment encoding said enzyme is prepared. This DNA fragment is ligated with a proper vector DNA fragment by means of, for example, DNA ligase, to construct a recombinant DNA containing at least one gene selected from xylose isomerase gene, xylulokinase gene, transaldolase gene and transketolase gene.

The donor microorganism used in the invention for such a DNA containing said gene or genes is subject to no special limitation but any can be used so long as it possesses xylose digesting ability. Whereas, microorganisms belonging to genera *Escherichia*, *Xanthomonas*, *Klebsiella*, *Rhodobacter*, *Flavobacterium*, *Acetobacter*, *Gluconobacter*, *Rhizobium*, *Abrobacterium*, *Salmonella* and *Pseudomonas* are conveniently used, in particular, *Escherichia coli* being preferred. Other *Escherichia* microorganisms; or those other than above-named and which have ability to digest xylose; or those which do not have xylose digesting ability due to, e.g., abnormality at promoter site or ribosome linkage site but code on their DNA structural genes of xylose isomerase, xyluloki-nase, transaldolase or transketolase, can also be used as donors of such a DNA which contains said gene(s). Furthermore, transformed microorganisms into which structural genes of xylose isomerase, xylulokinase, transaldolase or transketalase are introduced by such a technique as recombination of genes can also be used as donors of such DNA which contains such genes. It is also possible to ligate plural kinds of DNA fragments containing said genes obtained from different microorganisms to single vector.

The recombinant DNA containing at least one gene selected from xylose isomerase gene, xylulokinase gene, transaldolase gene and transketolase gene can construct a transformed microorganism which is capable of producing xylose isomerase, xylulokinase, transaldolase and/or transketolase, when it is introduced into a host microorganism belonging to genus *Zymobacter*. So introduced recombinant DNA may be incorporated in the genome of said *Zymobacter* host cells either in whole or in part, or may be present on the vector which is used for the transformation.

Separation and purification of the intended DNA from above donor microorganisms can be effected by any means known per se, for example, the method by Saito, Miura et al. (*Biochem. Biophys. Acta.*, Vol. 72, 619-629, 1963) or modifications thereof, or those using commercially available DNA extraction kits. Hereinafter a method following the one by Saito, Miura et al. is more specifically explained.

First, the donor microorganism is inoculated into a suitable liquid medium such as an yeast-starch medium containing 0.5% glycine (composition: yeast extract, 0.2%; soluble starch, 1.0%; pH 7.3), followed by culture under agitation at 4-60° C., preferably 30° C., for 8-48 hours, preferably for an overnight. After termination of the culture, the culture solution is subjected to a solid-liquid separation means, for example, centrifugation at 0-50° C., preferably 4° C., and at a rotation rate of 3,000-15,000 rpm, preferably 10,000 rpm.

Thus isolated microorganism cells are then suspended in a VS buffer (0.15M NaCl, 0.1M EDTA, pH 8.0). After addition of lysozyme, the suspension is allowed to stand at 4-45° C., preferably 37° C., for 0.5-4 hours, preferably an hour, to provide a protoplast liquid. To said liquid TSS buffer (0.1M TRIS, 0.1M NaCl, 1% SDS, pH 9.0) and 5M NaCl are added to dissolve the protoplast, followed by addition of a TE solution (10 mM TRIS, 1 mM EDTA, pH 8.0)-saturated phenol, to effect mild and sufficient suspension. The resultant suspension is centrifuged at 0-50° C., preferably 4° C., and at a rotation rate of 3,000-15,000 rpm, preferably 12,000 rpm, and the formed upper layer (aqueous phase) is suspended in chloroform. The suspension is centrifuged at 0-50° C., preferably 4° C. and at a rotation rate of 3,000-15,000 rpm, preferably 12,000 rpm. Thus formed upper layer (aqueous phase) is again suspended using phenol and chloroform.

Subsequently cold ethanol is added to the suspension, and whereupon formed opaque crude chromosome DNA is recovered. Said DNA is dissolved in SSC buffer (0.15M NaCl, 0.015M sodium citrate) and the solution is dialyzed against SSC buffer for an overnight. To the dialysate ribonuclease is added to a final concentration of 1-50 µg/ml, preferably 10 µg/ml, followed by standing at 4-45° C., preferably 37° C., for 0.5-16 hours, preferably 2 hours. Protease is further added to a final concentration of 0.1-10 µg/ml, preferably 1 µg/ml, followed by standing at 4-45° C., preferably at 37° C., for 15 minutes-8 hours, preferably 30 minutes. Similarly to the above, the system after the standing is treated with phenol and chloroform and dialyzed against SSC buffer to provide a purified chromosome DNA liquid of the donor microorganism.

Thus obtained donor microorganism's DNA is cleaved by, for example, restriction enzyme, and from which DNA fragments of sizes less than 1 kbp are removed by sucrose density gradient method. The remnant can be used as the donor DNA fragment. The restriction enzyme useful in that occasion is subject to no special limitation, but any of various enzymes such as AccII (also called FnuDII) which cleave DNA can be used. Besides the above enzymatic method, DNA can be cleaved by ultrasonic treatment or physical shearing force. A treatment of the donor DNA fragment ends with, for example, Klenow fragment or an enzyme such as DNA polymerase or mung bean nuclease in that occasion is preferred for improving subsequent laigation efficiency with vector DNA. Moreover, PCR-amplified products using donor microorganism's DNA or a fragment thereof as a template can also be used as the donor DNA fragments either as they are or after treating them as described above.

On the other hand, while vector DNA fragments are subject to no particular limitation, for example, pRK290, pMFY 40 or pMFY 31 derived from inter-Gram-negative bacterial broad host range plasmid, which are cleaved with restriction enzymes, are conveniently used. Vectors other than abovenamed, for example, broad host range plasmids of known Gram-negative bacteria, may be suitably selected and used. Useful restriction enzymes are not limited to those which produce adhesive ends but various other enzymes which cleave DNAs can be used. Furthermore, vector DNAs can also be cleaved by similar methods to those used for cleaving DNAs of said donor microorganisms.

Thus obtained vector DNA fragments may be treated with alkaline phosphatase in advance of their ligating reaction with aforesaid donor DNA fragments, to improve the ligation efficiency with said donor DNA fragments. Furthermore, when a donor DNA fragment is prepared by PCR amplification, its ligating efficiency can be improved by applying in advance a restriction enzyme site-imparting primer such as EcoRI to both ends of the amplified fragment, and by using a vector fragment which is cleaved with the same restriction enzyme which is used for cleaving the DNA fragment. The ligating reaction between the donor DNA fragment and vector DNA fragment can be conducted by conventionally practiced methods, for example, one using known DNA ligase. For instance, a recombinant DNA can be constructed in vitro by the action of a suitable DNA ligase, after annealing the involved donor DNA fragment and vector DNA fragment. Where necessary, furthermore, the annealed fragments may be introduced into a host microorganism and converted to a recombinant DNA, utilizing in vivo DNA-repairing ability.

As the host microorganism into which the recombinant DNA containing a donor DNA fragment and a vector DNA fragment is to be inserted, any that has ethanol fermentation ability and that can stably retain said recombinant DNA can be used. Whereas, microorganisms belonging to genus *Zymobacter*, generally *Zymobacter palmae*, are conveniently used in the present invention. Method for introducing such a recombinant DNA into the host microorganism is not particularly limited, but when *Zymobacter palmae* or the like is used as the host cell, introduction of the recombinant DNA utilizing electrical stimulation such as electroporation is preferred. Also as to ethanol-producing microorganisms other than *Zymobacter palmae*, for example, *Zymomonas mobilis*, yeast and other hosts, recombinant DNAs can be introduced thereinto by similar methods.

As a growth medium for so obtained transformed microorganisms, for example, where the host microorganism belongs to *Zymobacter*, RM media are frequently used. Where host microorganisms other than *Zymobacter*, such as *Bacillus subtilis*, yeast or the like are used, cultivation in various media suitable for individual host microorganisms can be conducted, and cultivation conditions such as culture temperature can also be suitably designed according to the properties of the used host microorganism. When the vector DNA fragment codes various antibiotic-resistant genes, addition of an adequate amount of a corresponding antibiotic to the medium enables more stable retention of the recombinant DNA which has been introduced. Furthermore, when the used vector DNA is one which codes a gene supplementing auxotrophicity of the host microorganism, stability of the recombinant DNA can similarly be improved by using a medium which contains none of the required nutrient.

The present invention provides a recombinant DNA which enables imparting to *Zymobacter* microorganisms xylose fermentation ability by recombinant DNA method; and transformed microorganisms containing the recombinant DNA fragment(s). Use of said transformed microorganisms enables efficient ethanol production from xylose-containing sugar solution as the feedstock.

Ethanol production from a xylose-containing sugar solution as the feedstock can be conducted through the steps of fermenting a saccharified feedstock containing xylose by the action of said pentose-fermentative transformed microorganism, and recovering ethanol from the resultant fermentation liquid, according to, for example, alcoholic fermentation method known per se, using a carrier on which said transformed microorganisms are immobilized.

Immobilization of the transformed microorganisms on said carrier can be effected by any of conventional techniques known per se, for example, entrapping, physical adsorption or covalent bonding.

As the carrier, those preferred have hollow, rugged or porous forms having a large surface area per unit volume, or can swell upon absorbing water, are fluidable and have particle sizes and specific gravity values which do not allow the carrier's easy flowing out of the reaction system. The carrier's configuration may be versatile, for example, special forms of plates, fibers or cylinders, sponge-like structures, particles, blocks or cubes. Of those, fine particles which allow easy ensuring of fluidability and sufficient surface area are preferred. As materials for the carrier, various organic and inorganic materials heretofore used as carrier materials for microorganisms or enzymes can be used, examples of which include inorganic materials such as granular activated carbon, crushed activated carbon, charcoal, zeolite, mica and sand; resin materials such as photo-hardenable resin, polyurethane, polyvinyl alcohol, polyethylene, polyacrylamide, polyester, polypropylene, agar, alginic acid, carrageenan, cellulose, dextran, agarose, ion-exchange resin and the like; porous ceramics such as silica gel; anthracite; and activated carbon or the like mixed in resinous material. These may be used either alone or in combination of two or more.

Said immobilization carriers are normally used as being filled in bioreactors. As bioreactors used for fermentation, there are continuously stirred tank type, packed bed type, membrane type, fluidized bed type and horizontal type, as classified by their operation system. Use of such bioreactors allows continuous fermentation and dispenses with supplying and recovery of the microorganisms, etc. and, therefore, is preferred.

In the occasion of said alcoholic fermentation, various nutrition sources for the microorganisms may be blended in the sugar solutions where necessary. For example, as nitrogen source, yeast extract, corn steep liquor, pepton, meat extract, bonito extract and the like can be used.

Hereinafter the invention is still more specifically explained referring to working examples, it being understood that the invention is not limited thereto.

EXAMPLES

Example 1

Construction of a Recombinant Plasmid DNA Containing *E. coli*-Derived Xylose Isomerase and Xylulokinase Genes

Figure 1:
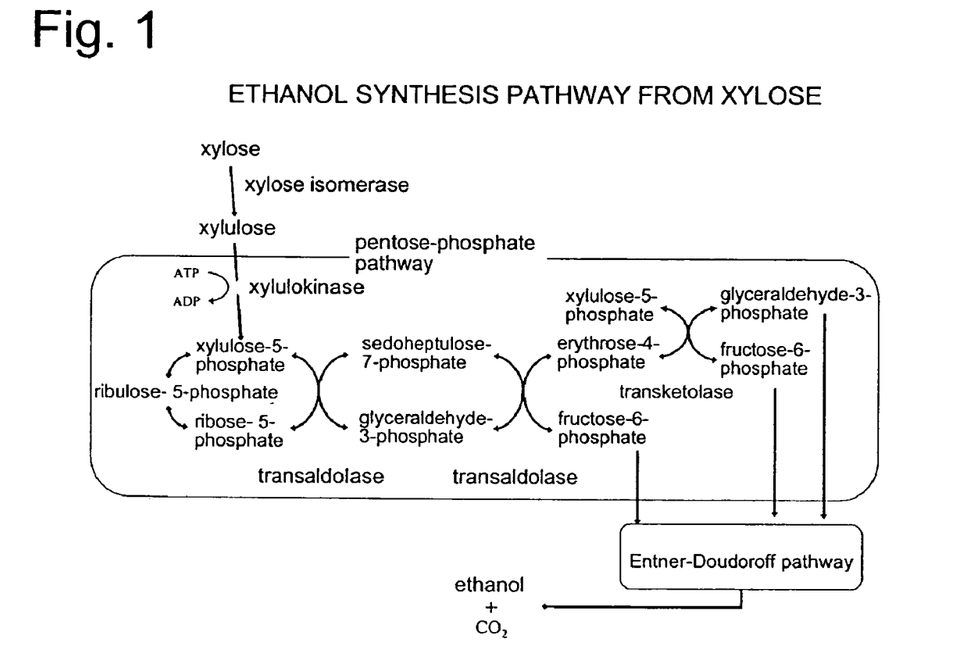
FIG. 1 shows ethanol biosynthesis pathway from xylose.

*Zymobacter palmae* is unable to ferment xylose. As the causes therefor, deficiency or low activity level in said bacterium of xylose isomerase which is an enzyme for converting xylose to xylulose; xylulokinase which is an enzyme catalyzing phosphatizing reaction of xylulose; and aldosereductase and transketolase which are key enzymes for leading the converted xylulose phosphate to biosynthesis of ethanol via pentose phosphate pathway. Therefore, it becomes possible to impart ethanol producing ability from xylose to the bacterium, by introducing thereinto these enzyme genes and allowing their expression (FIG. 1).

Accordingly, we cloned these enzyme genes from *E. coli* genome DNA by means of PCR. Furthermore, by expressing the introduced four kinds of enzyme genes in *Zymobacter palmae* cells, we utilized a promoter gene (GAP promoter) which controls expression of glyceraldehyde-3-phosphate dehydrogenase whose mass expression in *Zymomonas mobilis*, a bacterium said to be very closely akin to *Zymobacter palmae*, had been reported.

*E. coli*-derived xylose isomerase gene and xylulokinase gene were cloned by means of PCR. That is, *E. coli*-derived xylose isomerase gene and xylulokinase gene were inserted in tandem downstream of promoter gene of *Zymomonas mobilis*-derived glyceraldehyde-3-phosphate dehydrogenase gene, and for preparing DNA fragment to whose two ends EcoRI restriction enzyme cleavave sites for cloning were imparted, the following four kinds of PCR primers were designed based on known *Zymomonas mobilis*-derived glyceraldehyde-3-phosphate dehydrogenase gene sequence (*J. Bacteriol.* Vol.169 (12), 5653-5662, 1987) and known base sequences of *E. coli*-derived xylose isomerase gene and xylulokinase gene (*Appl. Environ. Microbiol.*, Vol.47 (1), 15-21, 1984):

```
ZGX1:                                    (SEQ ID NO. 1)
5'-CGGAATTCGTTCGATCAACAACCCGAATCCTATCG-3',

ZGX2:                                    (SEQ ID NO. 2)
5'-TACTGGAATAAATGGTCTTCGTTATGCAAGCCTATTTTGACCAGCCT
CGAT-3',

ZGX3:                                    (SEQ ID NO. 3)
5'-ATCGACTGGTCAAAATAGGCTTGCATAACGAAGACCATTTATTCCAG
TA-3',

EX4:                                     (SEQ ID NO. 4)
5'-CGGAATTCATGCATAGTTGCCAAAAGTTGCTGTCA-3'.
```

As the first PCR, using a genome DNA prepared from *Zymomonas mobilis* cell as the template, an about 300 bp DNA fragment comprising the promoter and N-end site of xylose isomerase gene was amplified with use of the primer ZGX1 and ZGX3. Separately, with *E. coli* genome DNA used as the template, an about 3.0 kbp DNA fragment comprising a part of the promoter gene, xylose isomerase gene and xylulokinase gene was amplified, using the primers ZGX2 and EX4.

Figure 2:
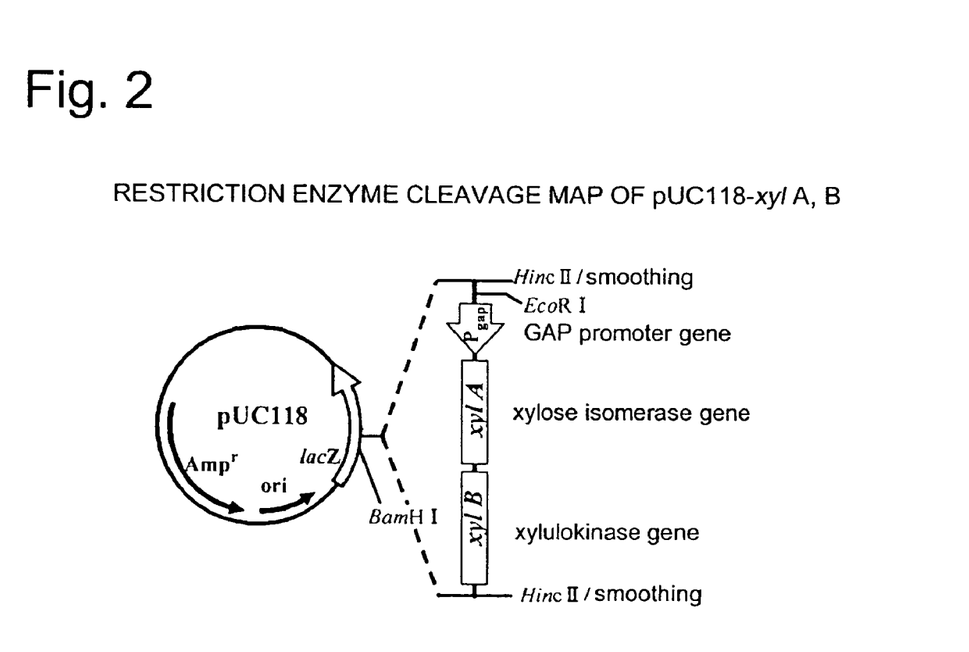
FIG. 2 shows a restriction enzyme cleavage map of a recombinant plasmid containing *Escherichia coli*-derived xylose isomerase gene and xylulokinase gene.

Then the DNA fragment containing the promoter gene and the DNA fragment containing xylose isomerase gene and xylulokinase gene were mixed, heated at 94° C. for 20 minutes, and maintained at 37° C. for 15 minutes to form a heteroduplex, which was reacted at 72° C. for 3 minutes in the presence of Taq DNA polymerase. Primer ZGX1 and primer EX4 were added to this reaction solution to carry out the second PCR, to amplify about 3.3 kbpDNA fragment in which GAP promoter gene, xylose isomerase gene, and xylulokinase gene were ligated by the order stated. After a smoothing reaction of both ends of this DNA fragment, the DNA fragment was mixed with a vector plasmid DNA for *E. coli* and HincII restriction enzyme cleaved fragments of pUC 118, and ligated by T4 ligase to construct a recombinant plasmid DNA. Using this recombinant plasmid, *E. coli* JM 109 was transformed following accepted procedures. Thereafter the transformed strain was applied onto a LB plate medium (1% Bacto Tripton, 0.5% yeast extract, 1% NaCl, 1.5% agar) containing 50 µg/ml of ampicillin, 0.1 mM isopropyl-β-D-thio-galactoside, and 20 µg/ml of 5-bromo-4-chloro-3-indolyl-β-D-galactopyranoside, to let it form a colony. The recombinant plasmid extracted from the transformed strain forming the white colony was named pUC118-xyl A, B (FIG. 2).

Example 2

Construction of a Recombinant Plasmid DNA Containing *E. coli*-derived Transaldolase and Transketolase Genes On *E. coli* genome DNA, transaldolase gene and transketolase gene do not form an operon but are conformed at mutually distant positions. Therefore, transaldolase and transketolase were individually cloned and linked to come under the control of *Zymomonas mobilis*-derived GAP promoter. For this purpose, the following four kinds of PCR primers were designed, based on known *Zymomonas mobilis*-derived glyceraldehyde-3-phosphate dehydrogenase gene sequence and known *E. coli*-derived transaldolase gene (*Nucleic Acids Res.*, Vol.20, 3305-3308, 1992):

```
ZGT1:                                    (SEQ ID NO. 5)
5'-CGCGGATCCGTTCGATCAACAACCGAATCCTATC-3',

ZGT2:                                    (SEQ ID NO. 6)
5'-CTTAATAAGTTAGGAGAATAAACATGACGGACAAATTGACCTCCCTT

CGT-3'

ZGT3:                                    (SEQ ID NO. 7)
5'-ACGAAGGGAGGTCAATTTGTCCGTCATGTTTATTCTCCTAACTTATT

AAG-3'

ETA4:                                    (SEQ ID NO. 8)
5'-CATTTTGACTACCAGATCTAGATTACAGCAGATCGCCGATCATTTTT

TCC-3'.
```

As the first PCR, using a genome DNA prepared from *Zymomonas mobilis* as the template, an about 300 bp DNA fragment comprising the promoter and N-end site of transaldolase gene, with Bam HI restriction enzyme cleavage site imparted upstream end of said promoter gene was amplified, using the primers ZGT1 and ZGT3. Separately, using *E. coli* genome DNA as the template, an about 1.2 kbpDNA fragment comprising a part of the promoter gene and transaldolase gene with XbaI restriction enzyme cleavage site imparted to C-end of said transaldolase gene was amplified using the primers ZGT2 and ETA4.

Then the DNA fragment containing the promoter gene and the DNA fragment containing transaldolase gene were mixed, heated at 94° C. for 20 minutes, and maintained at 37° C. for 15 minutes to form a heteroduplex, which was reacted at 72° C. for 3 minutes in the presence of Taq DNA polymerase. Primer ZGT1 and primer ETA4 were added to the reaction solution and second PCR was carried out to amplify about 1.3 kbpDNA fragment in which GAP promoter gene and transaldolase gene were ligated by the order stated. Subjecting the two ends of this DNA fragment to a smoothing reaction, the fragment was mixed with a vector plasmid DNA for *E. coli* and HincII restriction enzyme cleaved fragment of pUC118, and ligated by T4 ligase to construct a recombinant plasmid DNA.

Using this recombinant plasmid, *E. coli* JM109 (ATCC 53323) was transformed following the accepted practice. Thereafter the transformed strain was applied onto a LB plate medium (1% Bacto Tripton, 0.5% yeast extract, 1% NaCl, 1.5% agar) containing 50 µg/ml of ampicillin, 0.1 mM isopropyl-β-D-thio-galactoside and 20 µg/ml of 5-bromo-4-chloro-3-indolyl-β-D-galactopyranoside, to let it form a colony. The recombinant plasmid extracted from the transformed strain forming the white colony was named pUC118-tal. Then transketolase gene was amplified by means of PCR. Based on known base sequence of transketolase gene (*J. Bacteriol.*, Vol.174, 1707-1708, 1992), the following two primers were synthesized:

```
ETK1:                                    (SEQ ID NO. 9)
5'-CGGAATTCTCGAGCTCCAGTTACTCAATACGTAACAATAA-3',

ETK2:                                   (SEQ ID NO. 10)
5'-CGGCATGCCTCGAGGCAAACGGACATTATCAAGGTAATAAAAAAGGT

CGC-3'.
```

In the first PCR, from a genome DNA prepared from *E. coli* cell as the template, about 2.1 kbpDNA fragment was amplified, in which fragment XbaI restriction enzyme cleavage site was imparted upstream of N-end of transketolase gene and SphI restriction enzyme cleavage site, downstream of C-end thereof, using primers ETK1 and ETK2. Subjecting the two ends of this DNA fragment to a smoothing reaction, the fragment was mixed with a vector plasmid DNA for *E. coli* and HincII restriction enzyme cleaved fragment of pUC118, and ligated by T4 ligase to construct a recombinant plasmid DNA.

Using this recombinant plasmid, *E. coli* JM 109 was transformed following accepted procedures. Thereafter the transformed strain was applied onto a LB plate medium (1% Bacto Tripton, 0.5% yeast extract, 1% NaCl, 1.5% agar) containing 50 µg/ml of ampicillin, 0.1 mM isopropyl-β-D-thio-galactoside and 20 µg/ml of 5-bromo-4-chloro-3-indolyl-β-D-galactopyranoside, to let it form a colony. The recombinant plasmid extracted from the transformed strain forming the white colony was named pUC118-tkt.

Figure 3:
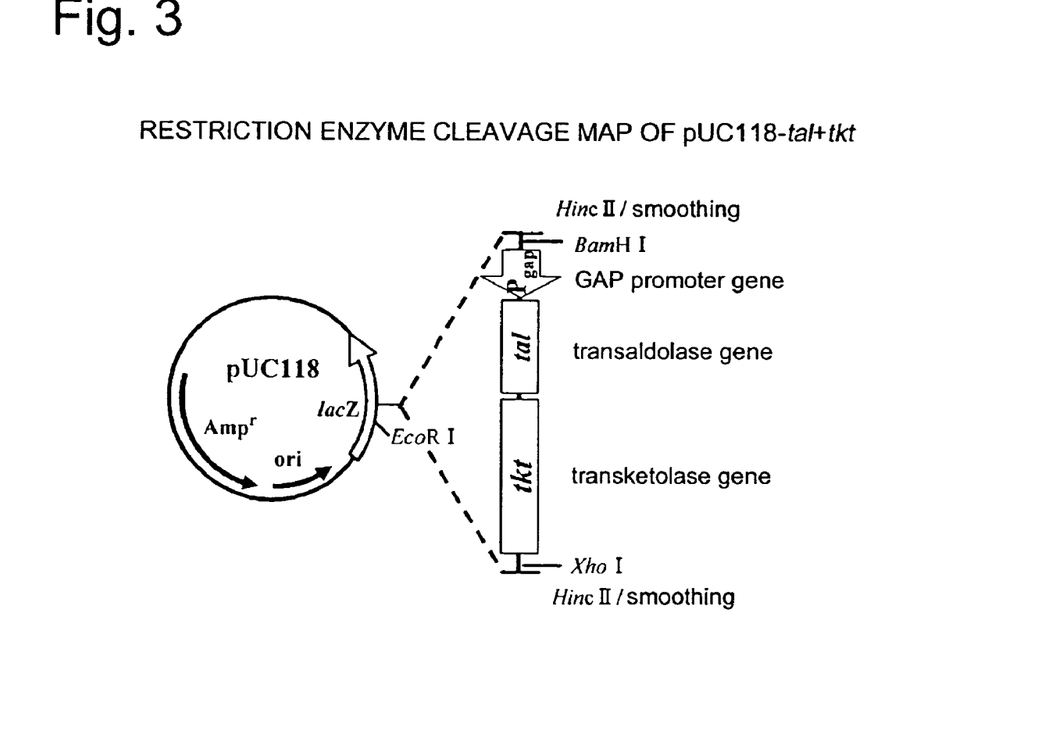
FIG. 3 shows a restriction enzyme cleavage map of a recombinant plasmid containing *Escherichia coli*-derived transaldolase gene and transketolase gene.

Then a recombinant plasmid containing a DNA fragment in which GAP promoter gene, transaldolase gene and transketolase gene were ligated was prepared. That is, DNA fragments provided by cleaving recombinant plasmid pUC118-tal at XbaI restriction enzyme cleavage site and SphI restriction enzyme cleavage site present in downstream region of C-end of the transaldolase gene in the plasmid, were mixed with approximately 2.1 kbpDNA fragment containing transketolase gene, which was provided by cleaving said recombinant plasmid pUC118-tkt with XbaI and SphI, and ligated by T4 ligase to synthesize a recombinant plasmid DNA. Using this recombinant plasmid, *E. coli* JM109 was transformed following accepted procedures, and the transformed strain was applied onto LB plate medium (1% Bacto Tripton, 0.5% yeast extract, 1% NaCl, 1.5% agar) containing 50 μg/ml of ampicillin to let it form a colony. Confirming that GAP promoter gene, transaldolase gene and transketolase gene were ligated to the recombinant plasmid extracted from the colony-forming transformed strain in tandem by the order stated, so constructed plasmid was named PUC118-tal-tkt (FIG. 3).

Example 3

Construction of Recombinant Plasmid DNA Containing Xylose-fermentative Gene For introducing and expressing four kinds of xylose metabolic enzyme genes in *Zymobacter palmae*, these genes were inserted into a broad host range plasmid vector to synthesize a recombinant plasmid.

Figure 4:
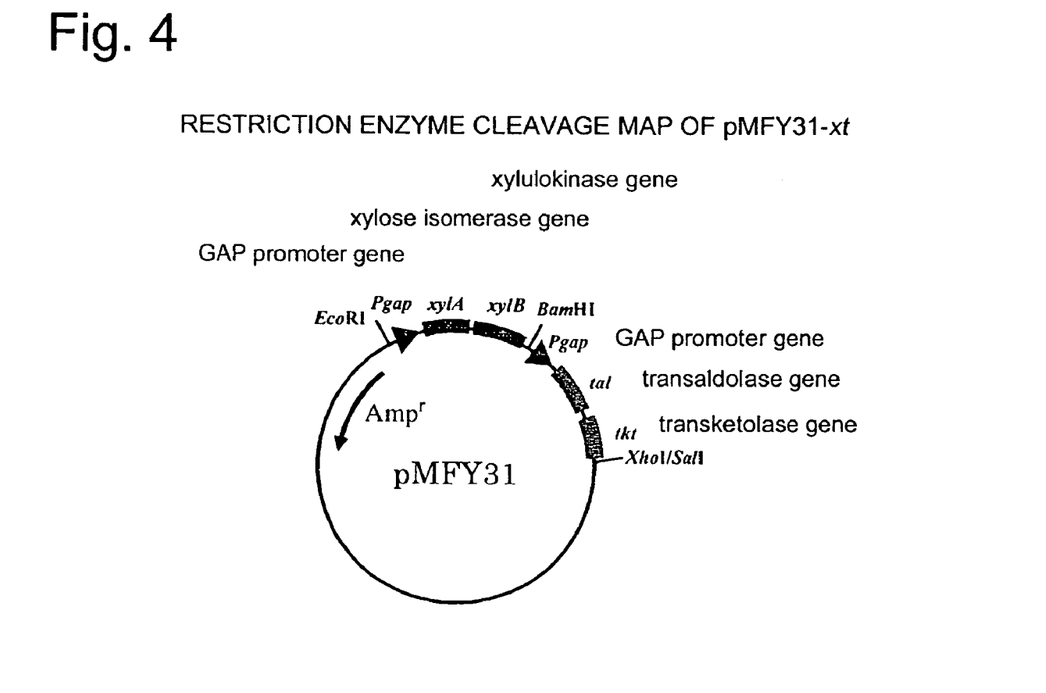
FIG. 4 shows a restriction enzyme cleavage map of a recombinant plasmid containing four kinds of xylose fermentative genes.

An about 3.4 kbpDNA fragment containing GAP promoter gene, xylose isomerase gene and xylulokinase gene was prepared by cleaving recombinant plasmid pUC118-xylA, B with EcoRI restriction enzyme and BamHI restriction enzyme. Also an about 3.3 kbpDNA fragment containing GAP promoter gene, transaldolase gene and transketolase gene was prepared by cleaving recombinant plasmid pUC118-tal+tkt with BamHI restriction enzyme and XhoI restriction enzyme. These two fragments were mixed with an about 11.6 kbpDNA fragment which was prepared by cleaving a broad host range vector plasmid pMFY 31 (*Agric. Biol. Chem*. Vol. 49 (9), 2719-2724, 1985) with EcoRI restriction enzyme and SalI restriction enzyme, and ligated by T4 ligase to construct a recombinant plasmid DNA. Using this recombinant plasmid, *E. coli* JM 109 was transformed following accepted procedures. Thereafter the transformed strain was applied onto a LB plate medium (1% Bacto Tripton, 0.5% yeast extract, 1% NaCl, 1.5% agar) containing 50 μg/ml of ampicillin, 0.1 mM isopropyl-β-D-thio-galactoside and 20 μg/ml of 5-bromo-4-chloro-3-indolyl-β-D-galactopyranoside, to let it form a colony. Confirming that GAP promoter, xylose isomerase gene, xylulokinase gene, GAP promoter, transaldolase gene and transketolase gene were ligated to the recombinant plasmid extracted from the colony-forming transformed strain by the order stated, the DNA was named pMFY31-xt (FIG. 4).

Example 4

Synthesis of Xylose-fermetative *Zymobacter palmae*

Recombinant plasmid pMFY31-xt which was constructed in *E. coli* was transformed into *Zymobacter palmae* (ATCC 51623).

*Zymobacter palmae* was statically cultured for an overnight in RM medium (2.0% glucose, 1.0% Bacto-yeast extract, 0.2% $KH_2PO_4$, pH 6.0). Five (5) ml of the pre-cultured liquid was subcultured in 50 ml of T medium (2.0% glucose, 1.0% Bacto-yeast extract, 1.0% $KH_2PO_4$, 0.2% $(NH_4)_2SO_4$, 0.05% $MgSO_4.7H_2O$, pH 6.0) at 30° C. for 90 minutes. The cultured liquid was centrifuged at 4° C., 300 rpm and for 10 minutes to isolate the microorganism cells to which 20 ml of cooled 10% glycerol was added, followed by suspension and washing. Conducting another centrifugation at 4° C., 3000 rpm for 10 minutes, competent cells were obtained. Two-hundred (200) μl of the competent cells and 10 μl of pMFY31-xtDNA solution were mixed on ice, transferred into a cuvette attached to an electroporation device, and electric pulse was applied thereto under such conditions as: voltage 200V, capacitance 250μ FD and resistance 200%. Immediately then 1 ml of T medium was added to the cuvette, the cells were statically cultured at 30° C. for an hour, and caused to form a colony on a selective medium. Xylose-formentative, transformed strain was selected on T agar plate medium (2.0% xylose, 1.0% Bacto-yeast extract, 1.0% $KH_2PO_4$, 0.2% $(NH_4)_2SO_4$, 0.05% $MgSO_4.7H_2O$, 1.5% agar, pH6.0) containing xylose as the sole carbon source and 100 μg/ml of ampicillin. Expression of the four kinds of enzyme genes in the cells of *Zymobacter palmae* transformed strain was confirmed. Thus obtained transformed strain has been deposited with National Institute of Advanced Industrial Science and Technology, International Patent Organism Depositary under deposition number of FERM P-19451 (which has been transferred to international deposition under Budapest Treaty since Jun. 30, 2004 and given deposition number of FERM BP-10048).

After culturing *Zymobacter palmae* [pMFY31-xt] in T medium, in vitro cell-free extract was prepared and activity levels of the four enzymes were measured (*Mol. Gen. Genet.*, Vol. 234, 201-210, 1992; *Methods Enzymol.*, Vol. 9, 499-505, 1966; *J. Bacteriol.*, Vol. 100, 1289-1295, 1969). Using *E. coli* and *Zymobacter palmae* [pMFY31] as control strains, activity measurements were conducted in the similar manner, and the results were compared. Xylose isomerase, xylulokinase, transaldolase and transketolase were effectively expressed in *Zymobacter palmae* cells and showed markedly higher activity levels compared with *E. coli* (Table 1).

TABLE 1

Expression of Xylose-fermentative Genes in Recombinant *Zymobacter palmae* Cells

| | Enzymatic Activity (mU/mg protein) | | | |
|---|---|---|---|---|
| Strain | Xylose isomerase | Xylulo-kinase | Trans-aldolase | Trans-ketolase |
| *Zymobacter palmae* [pMFY31] | 0.08 | 0.07 | 0.13 | 0.11 |
| *Zymobacter palmae* [pMFY31-xt] | 9.33 | 8.14 | 2.46 | 2.59 |
| *Escherichia coli* K12 | 3.23 | 2.78 | 1.85 | 1.39 |

1U of xylose isomerase: amount of the enzyme necessary for producing 1 μmol of xylulose per minute at 30° C.

1U of xylulokinase: amount of the enzyme necessary for consuming 1 μmol of xylulose per minute at 30° C.

1U of transaldolase: amount of the enzyme necessary for producing 1 μmol of glyceraldehyde-3-phosphate per minute at 30° C.

1U of transketolase: amount of the enzyme necessary for producing 1 μmol of glyceraldehyde-3-phosphate per minute at 30° C.

Figure 5:
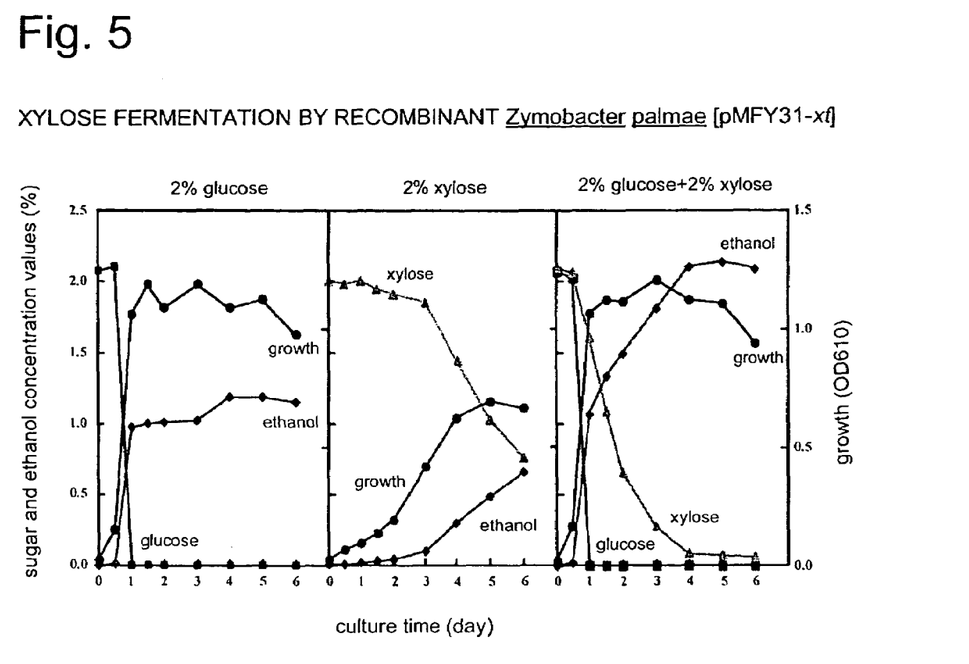
FIG. 5 is a graph demonstrating the result of ethanol production from xylose using recombinant *Zymobacter palmae* strain.

Great expression of the four kinds of enzymes attributable to introduction of pMFY31-xt having been confirmed, the recombinant strain was used for ethanol production from xylose. Fermentation ability using xylose as the sole carbon source was investigated. Inoculating the strains in the media each comprising 2% glucose, 2% xylose and 2% glucose+ xylose as the carbon source, the microbial growth and ethanol formation with time were measured (FIG. 5). In the medium wherein xylose was the sole carbon source, the growth rate dropped compared with that in the medium comprising glucose alone, but about 1% xylose was consumed by the 5th day of the culture to produce about 0.5% ethanol, and the yield was no less than 90%. In the glucose+xylose medium, residual xylose was almost nil on the 4th day of the culture, and ethanol production close to the theoretical yield was achieved. The improvement in xylose-fermentation ability in the mixed presence of glucose was remarkable, and the transformed strain could be evaluated as practically useful microorganisms for fermentation, upon optimization of bioreactors.

Example 5

Figure 6:
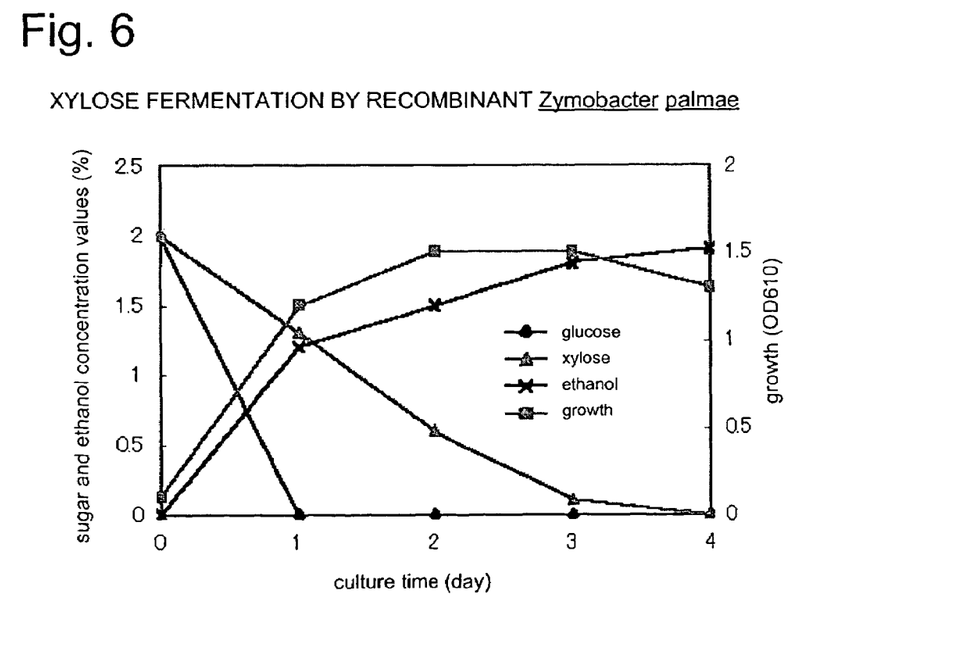
FIG. 6 is a graph demonstrating ethanol productivity in batch fermentation of xylose by recombinant *Zymobacter palmae* strain.

Recombinant *Zymobacter palmae* FERM P-19451 (BP-10048) strain was inoculated in GX medium (2.0% glucose, 2.0% xylose, 1.0% yeast extract, 1.0% $KH_2PO_4$, 0.2% $(NH_4)_2SO_4$, 0.05% $MgSO_4.7H_2O$, pH 6.0) using biomass partially saccharified liquid-derived glucose and xylose as the carbon source, and statically cultured for two days to provide a pre-culture solution. For the main culture the above GX medium was used, in which 10% to the main culture GX medium of said pre-culture solution was inoculated, followed by culturing under mild agitation at 30° C. Growth rate of the inoculated cells, glucose concentration, xylose concentration and ethanol concentration changes with time were regularly measured, to confirm that substantially all of the xylose was consumed by 3 days' culture and ethanol was produced at an yield close to the theoretical yield (FIG. 6).

Example 6

Using a medium prepared by adding yeast extract, $KH_2PO_4$, $(NH_4)_2SO_4$ and $MgSO_4.7H_2O$ to a sugar solution (12% glucose, 3% xylose) formed by sulfate saccharification of waste wood, in the amounts, respectively, of 1.0%, 1.0%, 0.2% and 0.05% to the sugar solution and adjusting pH to 6.0, continuous fermentation was conducted. Recombinant *Zymobacter palmae* FERM P-19451 (BP-10048) was immobilized on photo-hardenable resin ENTG™-3800 (manufactured by Kansai Paint) by entrapping. For the continuous fermentation a draft tube-formed bioreactor (fluidized bed type) was used. After throwing the immobilization carrier into the reactor at a fill ratio of 20%, the medium was continuously poured into the reactor from a lower part. A fluidized bed was formed by collecting the carbon dioxide formed by the fermentation and recycling it into the reactor from a lower part thereof. The continuous fermentation could be carried out at 30° C. and at a dilution ratio D equaling 0.1 $h_{-1}$ stably for more than a month, with the sugar consumption ratio not lower than 99% and ethanol yield not less than 95%.

Example 7

Continuous fermentation was conducted using a medium prepared by adding yeast extract, $KH_2PO_4$, $(NH_4)_2SO_4$ and $MgSO_4.7H_2O$ to a sugar solution (8% glucose, 3% xylose) formed by sulfate saccharification of rice straw, in the amounts, respectively, of 1.0%, 1.0%, 0.2% and 0.05% to the sugar solution and adjusting pH to 6.0. Recombinant *Zymobacter palmae* FERM P-19451 (BP-10048) cells were immobilized on cylindrical (2 mmφ×3 mm) polypropylene carrier which was thrown into the cell suspension. For the continuous fermentation a fixed bed bioreactor (packed bed type) was used. After throwing the immobilization carrier into the reactor at a fill ratio of 80%, said medium was continuously supplied into the reactor from a lower part. The continuous fermentation could be carried out at 30° C. and at a dilution ratio D equaling 0.2 $h_{-1}$ stably for more than a month, with the sugar consumption ratio not lower than 99% and ethanol yield not less than 95%.

Example 8

A test similar to Example 3 was run using two fixed bed bioreactors as used as the continuous fermentation apparatus in Example 7 coupled in series. In consequence, continuous fermentation could be stably conducted for more than a month, even under the condition of a dilution ratio D equaling 0.2 $h_-$, with the sugar consumption ratio not lower than 99% and ethanol yield not less than 95%.

The invention claimed is:

1. An isolated *Zymobacter palmae* strain transformed with a polynucleotide encoding xylose isomerase, wherein the polynucleotide is obtained from *Zymomonas mobilis* using PCR primers of SEQ ID NO: 1 and 3 and from *E.coli* JM109 using PCR primers of SEQ ID NO: 2 and 4.

2. A process for producing ethanol which comprises fermenting xylose-containing saccharification material using the isolated *Zymobacter palmae* strain transformed with a polynucleotide encoding xylose isomerase of claim 1, and recovering ethanol from the resultant fermented solution.

3. Immobilization carrier on which the isolated Zymobacter palmae strain transformed with a polynucleotide encoding xylose isomerase of claim 1 is immobilized.

4. A bioreactor equipped with the immobilization carrier of claim 3.

5. A process for producing ethanol, which comprises continuously fermenting xylose-containing saccharification material using the immobilization carrier of claim 3.

6. The isolated *Zymobacter palmae* strain of claim 1, which is FERM BP-10048.

* * * * *

```
SEQUENCE LISTING

<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 1
cggaattcgt tcgatcaaca acccgaatcc tatcg                              35

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 2
tactggaata aatggtcttc gttatgcaag cctattttga ccagcctcga t            51
```

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: Synthetic Construct

<400> SEQUENCE: 3
atcgactggt caaaataggc ttgcataacg aagaccattt attccagta            49

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic Construct

<400> SEQUENCE: 4
cggaattcat gcatagttgc caaaagttgc tgtca                           35

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic Construct

<400> SEQUENCE: 5
cgcggatccg ttcgatcaac aaccgaatcc tatc                            34

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic Construct

<400> SEQUENCE: 6
cttaataagt taggagaata aacatgacgg acaaattgac ctcccttcgt           50

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic Construct

<400> SEQUENCE: 7
acgaagggag gtcaatttgt ccgtcatgtt tattctccta acttattaag           50

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic Construct

<400> SEQUENCE: 8
cattttgact accagatcta gattacagca gatcgccgat cattttttcc           50

-continued

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 9
cggaattctc gagctccagt tactcaatac gtaacaataa                              40

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 10
cggcatgcct cgaggcaaac ggacattatc aaggtaataa aaaaggtcgc                   50